United States Patent [19]

Kato et al.

[11] Patent Number: 5,608,154
[45] Date of Patent: Mar. 4, 1997

[54] CARBON MONOXIDE SENSOR

[75] Inventors: Nobuhide Kato, Ama-gun; Yasuhiko Hamada, Nagoya, both of Japan

[73] Assignee: NGK Insulators, Ltd., Nagoya, Japan

[21] Appl. No.: 397,969

[22] Filed: Mar. 3, 1995

[30] Foreign Application Priority Data

Mar. 14, 1994 [JP] Japan .................................... 6-042704

[51] Int. Cl.$^6$ ........................ G01N 27/12; G01M 15/00; G08B 17/10
[52] U.S. Cl. ...................... 73/23.31; 73/23.2; 73/30.03; 73/31.06; 422/83; 422/94
[58] Field of Search ................................ 73/23.31, 31.06, 73/30.03, 23.2, 23.3, 23.24, 23.32; 422/83, 94

[56] References Cited

U.S. PATENT DOCUMENTS

| | | | |
|---|---|---|---|
| 4,277,323 | 7/1981 | Muller et al. | 204/195 |
| 4,574,627 | 3/1986 | Sakurai et al. | 73/116 |
| 4,718,999 | 1/1988 | Suzuki et al. | 204/406 |
| 4,820,386 | 4/1989 | Laconti et al. | 204/1 T |
| 4,944,273 | 7/1990 | Baresel et al. | 123/440 |
| 5,057,436 | 10/1991 | Ball | 436/113 |
| 5,168,068 | 12/1992 | Yanagisawa et al. | 436/134 |
| 5,252,949 | 10/1993 | Kirby et al. | 340/632 |
| 5,265,458 | 11/1993 | Usami et al. | 73/23.32 |
| 5,334,350 | 8/1994 | Friese et al. | 422/98 |
| 5,397,442 | 3/1995 | Wachsman | 204/153.16 |
| 5,476,001 | 12/1995 | Hoetzel et al. | 73/23.31 |
| 5,493,896 | 2/1996 | Riegel | 73/23.31 |

FOREIGN PATENT DOCUMENTS

| | | |
|---|---|---|
| 2617031A1 | 11/1977 | Germany . |
| 2918932C2 | 11/1979 | Germany . |
| 2909201C2 | 9/1980 | Germany . |
| 2922131A1 | 12/1980 | Germany . |
| 62-90529A | 4/1987 | Japan . |
| 2020824 | 11/1979 | United Kingdom . |
| 94/22007A1 | 9/1994 | WIPO . |

OTHER PUBLICATIONS

Lukacs et al., Solid State Ionics 68(1994) 93–98, "Electrochemical investigations of a carbon monoxide–oxygen sensor."

*Primary Examiner*—Hezron E. Williams
*Assistant Examiner*—J. David Wiggins
*Attorney, Agent, or Firm*—Ronald J. Kubovcik

[57] ABSTRACT

A carbon monoxide sensor (40) has a substrate arranged with other adjacent or overlaid layers attached thereon (41) defining a first space (43a) into which a unknown gas or gas mixture is introduced into and a second space (43b) communicating with the first space. A carbon monoxide adsorbent (61) is disposed in the second space, and an electrode (56) detects a partial pressure of oxygen in the carbon monoxide adsorbent. A pump cell includes the cell part (42), made of a solid electrolyte conducting oxygen ion, and a pair of electrodes (51, 52). The pump cell substantially removes oxygen from a gas in the first space (43a) while carbon monoxide in the gas is adsorbed onto the carbon monoxide adsorbent (61). Then, the pump cell introduces oxygen into the first space (43a), and a time is measured that the oxygen diffuses from the first space (43a) to the first detecting electrode (56) through the adsorbent (61). Only after an initial flow of the oxygen reacts with the carbon monoxide on the adsorbent (61), the oxygen reaches the first detecting electrode (56). Therefore, the time of transit across the adsorbent relates to an amount of the carbon monoxide in the gas. The carbon monoxide sensor is not affected by the concentration of oxygen in the gas, thereby improving accuracy in measuring the carbon monoxide concentration.

13 Claims, 5 Drawing Sheets

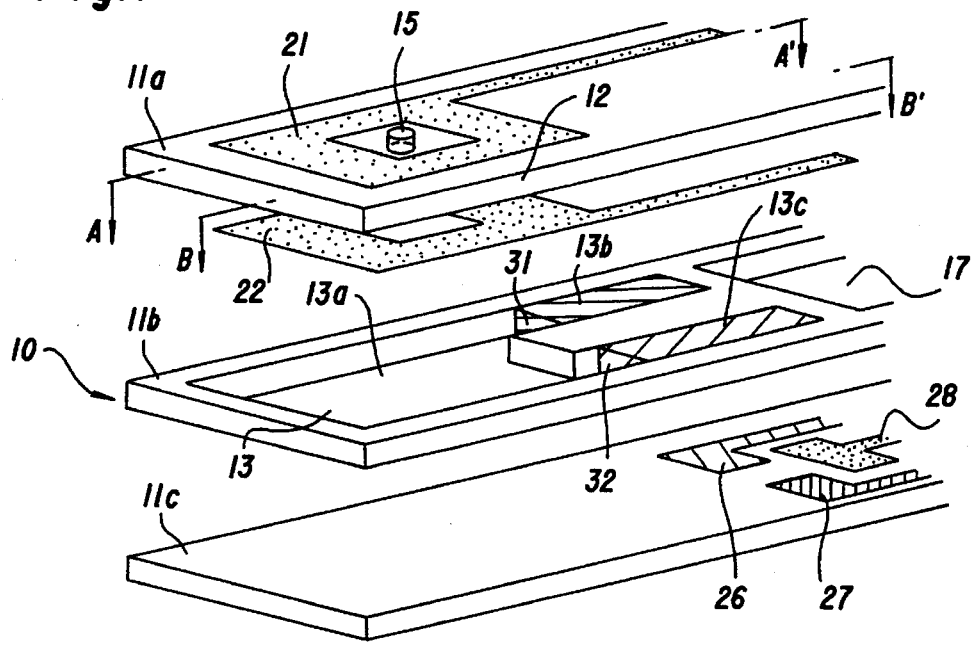
Fig.1
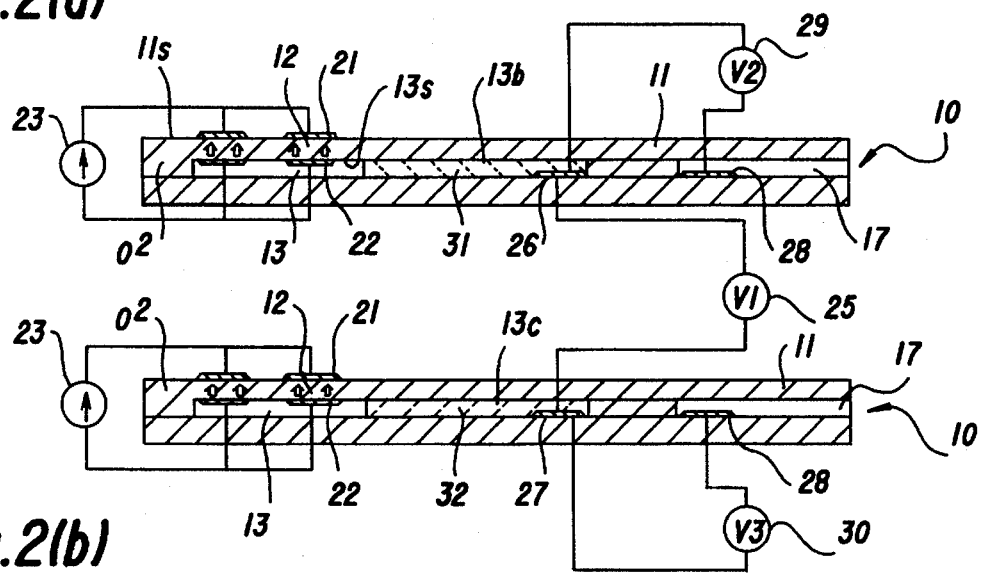
Fig.2(a)
Fig.2(b)

5,608,154

CARBON MONOXIDE SENSOR

BACKGROUND OF THE INVENTION

1. Field of the Invention

The present invention relates to a carbon monoxide sensor for detecting carbon monoxide in a gas, especially its concentration in the gas. The sensor of the present invention decreases an error caused by oxygen in a gas.

2. Description of Related Art

Carbon monoxide is a colorless, odorless, and toxic gas. A carbon monoxide sensor can be used industrially and domestically.

To detect a carbon monoxide concentration in an exhaust gas from an internal combustion engine is important since the concentration affects an air-to-fuel ratio of the internal combustion engine thereby affecting response thereof.

Japanese Patent Application hid-Open No. 2-91443 discloses a carbon monoxide sensor having a zirconia substrate, a pair of platinum electrodes, and another pair of gold electrodes. The sensor determines a carbon monoxide concentration based on a difference between a potential difference of the platinum electrodes and a potential difference of the gold electrodes. However, the sensor is influenced by a partial pressure of oxygen in a gas. Therefore, even though a carbon monoxide concentration is constant, the sensor may give a varying value of the carbon monoxide concentration depending on the partial pressure of oxygen.

SUMMARY OF THE INVENTION

An object of the present invention is to improve the accuracy of the carbon monoxide sensor by making the partial pressure of oxygen constant in the chamber of the sensor. The carbon monoxide sensor of the present invention includes a pump cell for removing an oxygen gas in a sample, thereby the oxygen in the sample does not affect the accuracy in carbon monoxide concentration.

One aspect of the present invention provides a carbon monoxide sensor comprising: a substrate arranged with other adjacent or overlaid layers attached thereon defining a space which an unknown gas or gas mixture to be measured is introduced into; a controlling means for controlling a partial pressure of oxygen in the space; an adsorbent, disposed in the space, for adsorbing carbon monoxide; and a first detecting means for detecting the partial pressure of oxygen in the space.

Another aspect of the present invention provides a method for detecting a concentration of carbon monoxide in a gas comprising the steps of: substantially removing an oxygen gas in the gas in a first space by a controlling means for controlling a partial pressure of oxygen in the first space so that a carbon monoxide in the gas is adsorbed onto an adsorbent for adsorbing carbon monoxide, said adsorbent being disposed in a second space that is connected to the first space; increasing a partial pressure of oxygen in the first space by the controlling means; measuring a time that the oxygen gas in the first space reaches a first detecting means for detecting a partial pressure of oxygen in said adsorbent; and convening the time into a carbon monoxide concentration in the gas.

Another aspect of the present invention provides a method for detecting a concentration of carbon monoxide in a gas comprising the steps of: substantially removing an oxygen gas in the gas in a first space by a controlling means for controlling a partial pressure of oxygen in the first space so that a carbon monoxide in the gas is adsorbed onto an adsorbent for adsorbing carbon monoxide, said adsorbent being disposed in a second space that is connected to the first space; increasing a partial pressure of oxygen in the first space by the controlling means; measuring a time difference between a time that the oxygen gas in the first space reaches a first detecting means for detecting a partial pressure of oxygen in said adsorbent and a time that the oxygen gas in the first space reaches a second detecting means for detecting a partial pressure of oxygen in a third space that is connected to the first space; and convening the time difference into a carbon monoxide concentration in the gas.

BRIEF DESCRIPTION OF THE DRAWINGS

FIG. 1 is an exploded perspective view of one embodiment of a carbon monoxide sensor of the present invention.

FIG. 2 (a) is a sectional view cut along the line A–A' in FIG. 1, and FIG. 2 (b) is a sectional view cut along the line B–B' in FIG. 1.

FIG. 3 (a) shows the concentration (%) of oxygen in a first space, FIG. 3 (b) shows an amount of carbon monoxide adsorbed by a carbon monoxide adsorbent, FIG. 3 (c) shows electromotive force of a first detecting electrode, FIG. 3 (d) shows electromotive force of a second detecting electrode 27, and FIG. 3 (e) shows a potential difference between the first detecting electrode 26 and the second detecting electrode 27.

DETAILED DESCRIPTION OF THE PREFERRED EMBODIMENTS

Figure 5:
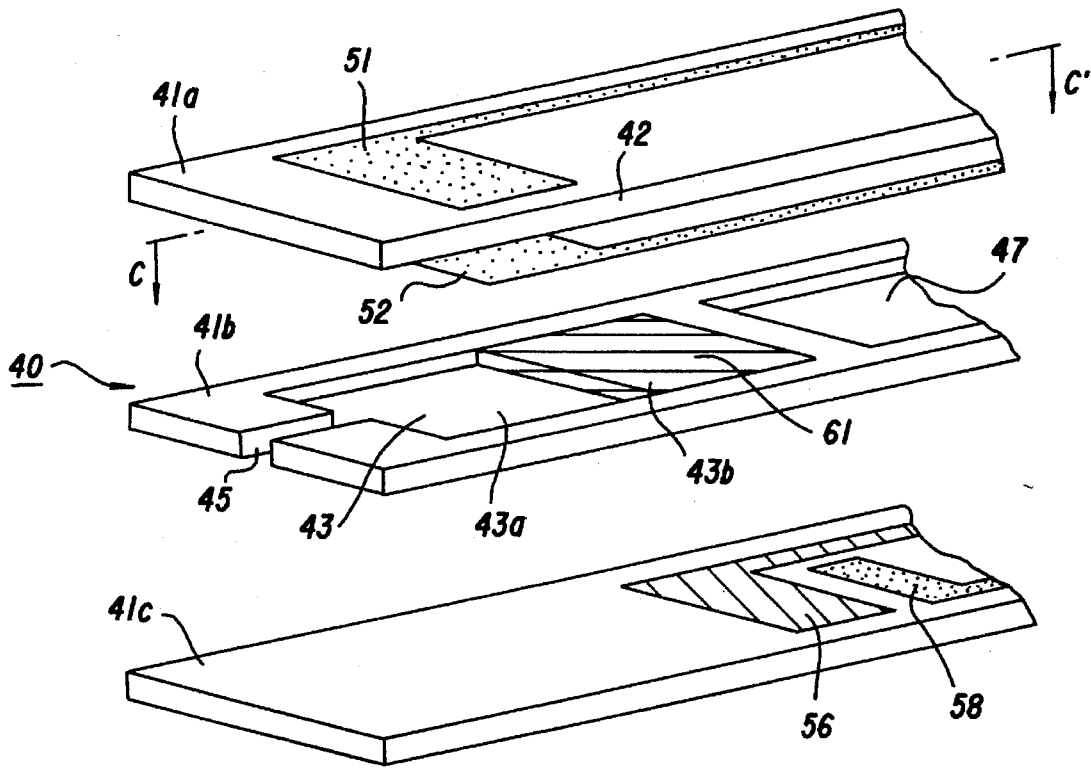
FIG. 5 is an exploded perspective view of another embodiment of the carbon monoxide sensor of the present invention.
Figure 6:
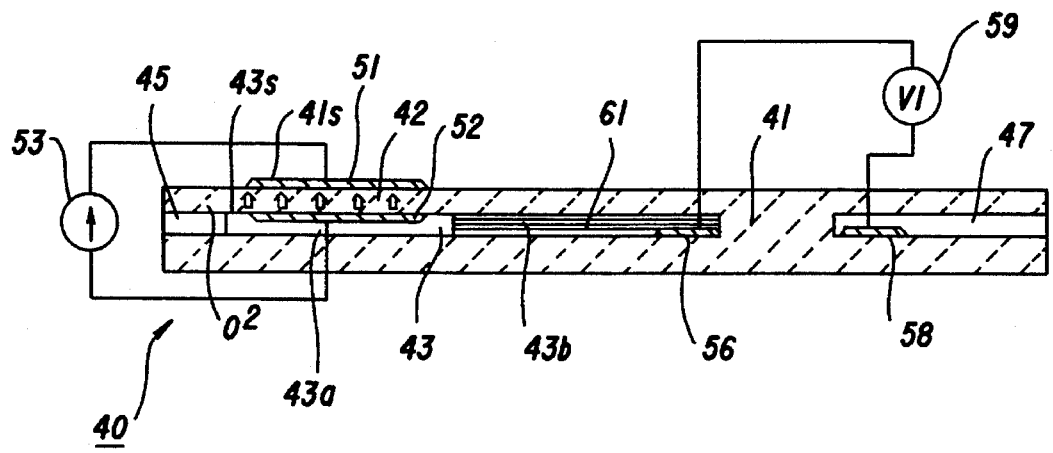
FIG. 6 is a sectional illustrative view of the carbon monoxide sensor cut along the line C–C' in FIG. 5.

In FIG. 5 and FIG. 6, a carbon monoxide sensor 40 has a substrate 41 defining a chamber 43 therein, electrodes 51, 52, a first detecting electrode 56, and a reference electrode 58.

The substrate 41 may be made by the steps of forming three sheets 41a, 41b, 41c and integrating the three sheets into a unitary structure. The three sheets may be made by doctor-blading, and the three green sheets may be laminated together, pressed, and then fired. Alternatively, the three sheets may be integrated by glass bonding.

The substrate 41 is formed of a chamber 43 inside. The chamber 43 includes the first space 43a and the second space 43b. The first space 43a is connected to a space outside of the substrate through an aperture 45 so as to introduce a gas to be measured into the space 43a. The aperture 45 determines a diffusion rate of a gas to be measured into the chamber 43.

The first space 43a is connected to the second space 43b. A carbon monoxide adsorbent 61 occupies the second space 43b. The carbon monoxide adsorbent 61 covers a first detecting electrode 56 so that a gas to be measured passes through the carbon monoxide adsorbent 61 and is then detected by the first detecting electrode 56.

A cell part 42 is a part of the substrate 41. A pump cell includes the cell part 42 and a pair of electrodes 51, 52, and the pump cell controls a partial pressure of oxygen at the first space 43a. The cell part 42 is placed between the pair of electrodes so that oxygen ion may permeate the cell part 42.

The cell part 42 is composed of a solid electrolyte conducting oxygen ion. The solid electrolyte includes, for example, partially stabilized zirconia and fully stabilized zirconia, which consists essentially of zirconium oxide and a stabilizer such as calcium oxide, magnesium oxide, yttrium oxide, scandium oxide, ytterbium oxide, cerium oxide, etc. Sheet 41a may be composed of the solid electrolyte.

The electrode 51 is coated onto an outer surface 41s of the sheet 41a so as to be exposed to atmosphere. The other electrode 52 is coated onto an inner surface 43s of the sheet 41a. Preferably, the electrode 52 has a shape corresponding to the electrode 51 by means of the cell pan 42. The electrodes 51, 52 may be a film. The film may be composed of a metal including, for example, platinum. The film may be a cermet screen printed by a paste mixture of a metal, such as platinum and a ceramic, such as zirconia.

In the pump cell, an electrical source applies direct current onto a pair of electrodes 51, 52 so that an oxygen gas in the chamber 43 transfers into a space outside of the substrate through the cell part 42. The oxygen gas in the chamber 43 changes into an oxygen ion at an interface of an inner surface 43s and the electrode 52, and the oxygen ion moves through the cell part 42. Then, the oxygen ion changes into an oxygen gas at an interface of an outer surface 41s and the electrode 51. On the other hand, the reaction can be reversed by changing the direction of the applied direct current. Upon applying direct current in the reverse direction, an oxygen gas in the space outside of the substrate transfers into the chamber 43 through the cell part 42. The oxygen gas in the space outside of the substrate changes into an oxygen ion at an interface of the outer surface 41s and the electrode 51, and the oxygen ion moves through the cell part 42. Then, the oxygen ion changes into an oxygen gas at an interface of the inner surface 43s and the electrode 52.

A first detecting electrode 56 acts as a first detecting device for detecting a partial pressure of oxygen in the second space 43b. An adsorbent 61 for adsorbing carbon monoxide fills the second space 43b of the chamber. The first electrode 56 is coated onto an inner surface 43s of the substrate 41. The first detecting electrode 56 is covered by a carbon monoxide adsorbent 61 so as to detect a partial pressure of oxygen in the carbon monoxide adsorbent 61. The first detecting electrode may include at least one of platinum and gold.

The carbon monoxide adsorbent 61 is preferably porous. A material for the adsorbent 61 is not limited, provided that the material adsorbs carbon monoxide. The adsorbent contains, for example, porous $ZnO$, $SnO_2$, $Al_2O_3$, etc. The adsorbent may be made of a porous mixture of $CuO$ and $ZnO$.

The substrate 41 defines a cavity 47 extending inside the substrate 41, and the cavity 47 is exposed to a gas other than the gas to be measured, for example, the atmosphere. Therefore, the cavity 47 is preferably formed apart from the aperture 45. A reference electrode 58 is arranged on an inner surface of the cavity 47. A voltmeter 59 for measuring a potential difference between the reference electrode 58 and the first detecting electrode 56 is connected to the reference electrode 58 and the first detecting electrode 56.

A heater not shown for controlling temperatures of the cell part 42 and the first detecting electrode 56 is preferably buried inside the substrate 41. Leads extend from the electrodes 51, 52, the first detecting electrode 56 and the reference electrode 58, and they can be connected to terminal pads which are not shown.

The usage of the carbon monoxide sensor 40 of the present invention is described hereinafter.

An oxygen gas is substantially removed from the gas in the first space 43a by the pump cell while carbon monoxide in the gas is adsorbed onto the carbon monoxide adsorbent 61. Subsequently, the oxygen gas is introduced into the first space 43a by the pump cell, and a flow time is measured over which direction the oxygen gas flows from the first space 43a to the first detecting electrode 56.

The measured flow time determines the concentration of carbon monoxide. The oxygen gas reacts with the carbon monoxide adsorbed onto the carbon monoxide adsorbent 61. Therefore, after an initial flow of the oxygen gas is consumed by the reaction, a subsequent flow of the oxygen gas reaches the first detecting element 56. In other words, the more carbon monoxide adsorbed, the longer it takes for oxygen gas flow to reach the first detecting element 56. This flow time is correlated with the concentration of carbon monoxide, and hence the measurement of the flow time relates to the measurement of the concentration of carbon monoxide.

In FIG. 3., firstly, a gas to be measured is introduced into the chamber 43 through the aperture 45. Then, at time $t_o$, a direct current from a power source 53 is applied to the electrodes 51, 52 so as to start removing the oxygen gas in the gas in the first space 43a of the chamber 43. The oxygen gas is substantially removed from the first space 43a so as to prevent carbon monoxide from reacting with oxygen on a surface of the carbon monoxide adsorbent 61. As a consequence, a partial pressure of oxygen in the first space 43a of the chamber 43 may become, for example, not more than $10^{-10}$, preferably not more than $10^{-2}$, with respect to the total pressure of the first space 43a. The partial pressure of oxygen may become about $10^{-30}$ in certain most favorable cases.

The oxygen gas reacts with carbon monoxide on the adsorbent 61 so as to give carbon dioxide. Therefore, as shown in FIG. 3 (b), the decrease in the oxygen gas increases an amount of carbon monoxide adsorbed onto the adsorbent 61. The increased carbon monoxide is correlated with the concentration of carbon monoxide in the gas.

A part of the gas from which the oxygen gas content has been substantially removed next diffuses from the first space 43a into the carbon monoxide adsorbent 61, and then reaches the first detecting electrode 56. At the first detecting electrode 56, an electromotive force, which can be expressed by the Nernst's equation, is generated on the basis of a difference between the partial pressure of oxygen at the reference electrode 58 and the partial pressure of oxygen at the detecting electrode 56.

After the gas has sufficiently diffused into the second space 43b so as to reach equilibrium, the carbon monoxide adsorbent 61 adsorbs an equilibrium amount of the carbon monoxide.

At time $t_1$ under equilibrium, the pump cell is operated so as to introduce an oxygen gas so that the first space 43a is brought into predetermined lean conditions. For example, in FIG. 3 (a), the oxygen gas concentration in the first space 43a changes from 0% to 1% at the time $t_1$.

The oxygen gas in the first space 43a diffuses into the carbon monoxide adsorbent 61 so as to reach the first detecting electrode 56. In the diffusion step, the oxygen gas reacts with carbon monoxide adsorbed onto the carbon monoxide adsorbent 61 to form carbon dioxide, consuming the oxygen gas. Therefore, the consumption of the oxygen gas with the adsorbed carbon monoxide delays the flow time that the oxygen gas reaches the first detecting electrode 56. The time lag depends upon an amount of carbon monoxide adsorbed onto the carbon monoxide adsorbent 61, and the amount of carbon monoxide adsorbed depends upon the concentration of carbon monoxide in the gas to be measured.

For example, in FIG. 3 (c), the electromotive force of the first detecting electrode 56 decreases to 400 mV at time $t_3$ once oxygen gas contacts the electrode. Then, a difference $t_c$ between the time $t_3$ and the time $t_1$ is calculated.

Figure 7:
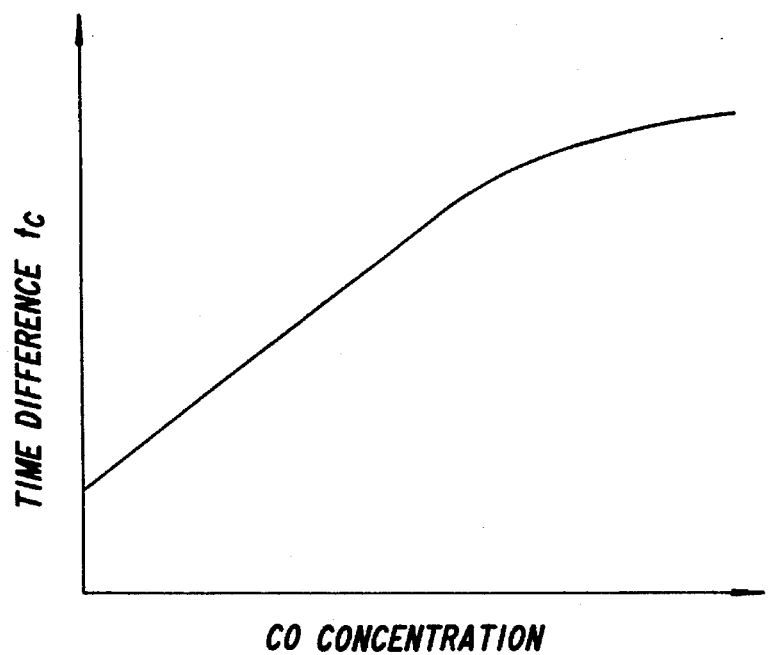
FIG. 7 is a graph showing a relation between the concentration of carbon monoxide and a time difference $t_c$ in the carbon monoxide sensor of FIG. 5.

FIG. 7 shows the correlation of the time difference $t_c$ with the concentration of the carbon monoxide in the gas. As the carbon monoxide concentration increases, the time difference $t_c$ increases. Using the correlation as a calibration curve, the time difference $t_c$ determines the concentration of carbon monoxide in the gas.

In FIG. 3 (b), the mount of carbon monoxide adsorbed onto the carbon monoxide adsorbent 61 begins to decrease at the time $t_1$. However, the immediate response of the measured electromotive force at the first electrode can happen only in theory. In the actual carbon monoxide sensor, it takes time from the time $t_1$ when the oxygen concentration starts to increase to a time when an amount of adsorbed carbon monoxide starts to decrease before the sensor can respond to the new lower carbon monoxide concentration, and the time lag corresponds to the diffusion of the oxygen gas from the first space 43a into the carbon monoxide adsorbent 61.

In FIG. 1, another embodiment of the present invention is described. FIG. 1 is an exploded perspective view of a carbon monoxide sensor 10 of the present invention. FIG. 2 (a) is a cross sectional view cut along the line A-A' in FIG. 1, and FIG. 2 (b) is a cross sectional view cut along the line B-B' in FIG. 1.

The carbon monoxide sensor 10 has a substrate 11 formed with a chamber 13, electrodes 21, 22, a first detecting electrode 26, a second detecting electrode 27 and a reference electrode 28. In the present embodiment of a carbon monoxide sensor 10, elements different from those of the carbon monoxide sensor 40 will be mainly described.

The substrate 11 has an integral structure, as the substrate 41. The substrate 11 defines the chamber 13 inside thereof. The chamber 13 includes a first space 13a, a second space 13b, and a third space 13c. The first space 13a communicates with the ambiance through an aperture 15 formed on the substrate 11 so as to introduce a sample gas to the first space 13a of the chamber 13. The aperture 15 determines a diffusion rate of the gas into the chamber 13.

The second space 13b and the third space 13c are separated from each other, and they communicate with the first space 13a. A carbon monoxide adsorbent 31 fills at least a part of the second space 13b, and a first detecting electrode 26 is covered by the carbon monoxide adsorbent 31. A partial pressure of oxygen in the gas that has passed through the carbon monoxide adsorbent 31 can be detected by the first detecting electrode 26. Preferably, the carbon monoxide adsorbent 31 fills the whole second space 13b. Similarly, a gas equilibrium member 32 fills at least a part of the third space 13c, and a second detecting electrode 27 is covered by the gas equilibrium member 32. A partial pressure of oxygen in the gas that has passed through the gas equilibrium member 32 can be detected by the second detecting electrode 27. Preferably, the gas equilibrium member 32 fills the whole third space 13c. The carbon monoxide sensor 10 of the present invention determines a carbon monoxide concentration by the fact that an amount of carbon monoxide adsorbed onto the carbon monoxide adsorbent 31 depends upon the concentration of carbon monoxide in the gas.

As is the case with the pump cell of the carbon monoxide sensor 40, a pump cell of the carbon monoxide sensor 10 has a pair of electrodes 21, 22 and a cell part 12, which is a part of the substrate 11. The pump cell can control the concentration of oxygen in the first space 13a. The cell part 12 is placed between the pair of electrodes 21, 22 so that oxygen ions may permeate the cell part 12. In FIG. 1, the cell part 12 is formed around the aperture 15. The electrodes 21, 22 and a power source 23 are similar to the electrodes 51, 52 and the power source 53, respectively, of the previous sensor embodiment.

The first detecting electrode 26 for detecting the partial pressure of oxygen in the second space 13b is arranged on an inner surface of a solid electrolyte so that the first detecting electrode 26 can detect the partial pressure of oxygen in the gas that has passed through the carbon monoxide adsorbent 31. Similarly, the second detecting electrode 27 for detecting the partial pressure of oxygen in the third space 13c is arranged on an inner surface of a solid electrolyte so that the second detecting electrode 27 can detect the partial pressure of oxygen in the gas that has passed through the gas equilibrium member 32. Furthermore, voltmeter 25 for measuring a potential difference between the first detecting electrode 26 and the second detecting electrode 27 is preferably disposed.

In the carbon monoxide sensor 10 of the present invention, the difference between a time when the gas reaches the first detecting electrode 26 through the carbon monoxide adsorbent 31 and another time when the gas reaches the second detecting electrode 27 through the gas equilibrium member 32 is important. Therefore, the shape of the second space 13b is preferably the same as that of the third space 13c, and it is also preferred that the second space 13b and the third space 13c are substantially symmetric with respect to the first space 13a. Moreover, the position of the first detecting electrode 26 is preferably substantially symmetric with respect to that of the second detecting electrode 27, and the diffusion resistance of the carbon monoxide adsorbent 31 to oxygen is preferably substantially equal to that of the gas equilibrium member 32 to oxygen. Preferably, the detecting electrode is made of a material containing a metal serving as an oxidizing catalyst, for example, platinum. Alternatively, a material containing gold may be used. The carbon monoxide adsorbent 31 corresponds to the carbon monoxide adsorbent 61.

The gas equilibrium member 32 is suitably made of a ceramic material that scarcely adsorbs carbon monoxide. The member 32 is preferably porous. In general, carbon monoxide is adsorbed more or less onto a surface of any ceramic material. A ceramic material adsorbing a sufficiently small amount of carbon monoxide is used for the ceramic material for the gas equilibrium member. The ceramic material for the gas equilibrium member is unsuitable for the carbon monoxide adsorbent. The gas equilibrium member may be made of, for example, porous $ZrO_2$.

The diffusion resistance of the gas equilibrium member 32 to oxygen is preferably substantially equal to that of the carbon monoxide adsorbent 31 to oxygen so as to decrease a difference between a time when the gas reaches the first detecting electrode 26 and a time when the gas has reached the second detecting electrode 27.

A cavity 17 and a reference electrode 28 corresponds to the cavity 47 and the reference electrode 58, respectively. A voltmeter 29 for measuring a potential difference between the reference electrode 28 and the first detecting electrode 26 is disposed, and another voltmeter 30 for measuring a potential difference between the reference electrode 28 and the second detecting electrode 27 is disposed.

A heater (not shown) for controlling temperatures of the cell part 12, the first detecting electrode 26 and the second detecting electrode 27 is preferably buried inside the substrate 11.

The usage of the carbon monoxide sensor 10 of the present invention will be described hereinafter. The concentration of carbon monoxide can be measured as follows. Initially, the chamber 13 has a rich atmosphere in which the concentration of oxygen is low, and a potential difference between the first detecting electrode 26 and the second detecting electrode 27 is monitored. Afterward, the rich atmosphere is changed into a lean atmosphere in which the concentration of oxygen in the chamber 13 is high, and a difference in time is detected between a time when the oxygen gas reaches the first detecting electrode 26 and a time when the oxygen gas reaches the second detecting electrode 27. There arc two methods for detecting the time difference. One method is to monitor a potential difference between the first detecting electrode 26 and the second detecting electrode 27. The other method is to monitor the electromotive force of the first detecting electrode 26 relative to the reference electrode 28 and the electromotive force of the second detecting electrode 27 relative to the reference electrode 28.

In FIG. 3., the gas to be measured is introduced into the chamber 13 through the aperture 15. After an equilibrium has reached, in an ideal case, the partial pressure of oxygen at the first detecting electrode 26 is substantially equal to the partial pressure of oxygen at the second detecting electrode 27, thereby the electromotive forces of both the electrodes are substantially equal to each other and the potential difference between both the electrodes is very small.

At time $t_o$, a direct current from the power source 23 is applied to the electrodes 21, 22 so as to start removing the oxygen gas from the gas in the first space 13a of the chamber 13. The oxygen gas is removed to such a degree that carbon monoxide cannot react with oxygen on a surface of the carbon monoxide adsorbent 31. In consequence, the partial pressure of oxygen in the first space 13a of the chamber 13 becomes, for example, not more than $10^{-15}$, preferably not more than $10^{-20}$, with respect to the total pressure of the first space 13a. This partial pressure of oxygen becomes about $10^{-30}$ in certain most favorable case.

The oxygen gas reacts with carbon monoxide adsorbed onto the carbon monoxide adsorbent 31 to form carbon dioxide. The concentration of the oxygen gas decreases so that the amount of carbon monoxide adsorbed onto the carbon monoxide adsorbent 31 increases, as shown in FIG. 3 (b). The increased carbon monoxide is correlated with the concentration of carbon monoxide in the gas.

A part of the gas from which the oxygen gas content has been substantially removed then diffuses from the first space 13a into the carbon monoxide adsorbent 31, reaching the first detecting electrode 26. On the other hand, the other part of the gas diffuses into the gas equilibrium member 32, reaching the second detecting electrode 27. Accordingly, in the first detecting electrode 26, electromotive force, which can be expressed by the Nernst's equation, is generated on the basis of a difference between the partial pressure of oxygen at the reference electrode 28 and the partial pressure of oxygen in the first detecting electrode 26. Similarly, in the second detecting electrode 27, electromotive force is generated relative, to the reference electrode 28.

After the gas has sufficiently diffused into the second space 13b and the third space 13c, reaching an equilibrium, the partial pressure of oxygen at the first detecting electrode 26 is substantially equal to the partial pressure of oxygen at the second detecting electrode 27 so that the electromotive force of the first detecting electrode 26 is substantially equal to the electromotive force of the second detecting electrode 27. Under the equilibrium, the carbon monoxide adsorbent 31 adsorbs carbon monoxide, while the gas equilibrium member 32 scarcely adsorbs carbon monoxide.

At time $t_1$ under the equilibrium, the pump cell is operated so as to introduce the oxygen gas, thereby the first space 13a is brought into a predetermined lean condition. For example, in FIG. 3 (a), the concentration of the oxygen gas in the first space 13a changes from 0% to 1% at the time $t_1$ so as to provide an oxygen flow to be measured according to transit time across the sensor volume space.

A part of the oxygen gas in the first space 13a diffuses into the carbon monoxide adsorbent 31, reaching the first detecting electrode 26. In the diffusion step, the oxygen gas reacts with carbon monoxide adsorbed onto the carbon monoxide adsorbent 31 to form carbon dioxide. Thus, an initial flow of the oxygen gas is consumed by the reaction. Therefore, the more the carbon monoxide adsorbed onto the adsorbent 31, the longer it takes for the oxygen flow or diffusion to reach the detecting electrode 26.

On the other hand, the other part of the oxygen gas in the first space 13a diffuses into the gas equilibrium member 32 and then reaches the second detecting electrode 27. The gas equilibrium member 32 scarcely adsorbs carbon monoxide, and hence the oxygen gas reaches the second detecting electrode 27 promptly without being consumed by the reaction.

Therefore, a difference between a time when the oxygen gas reaches the first detecting electrode 26 and a time when the oxygen gas reaches the second detecting electrode 27 depends upon the amount of carbon monoxide adsorbed onto the carbon monoxide adsorbent, and this amount of adsorbed carbon monoxide depends upon the concentration of carbon monoxide in the gas to be measured.

The difference between the times when the oxygen gas has reached the first detecting electrode 26 and the second detecting electrode 27 can be obtained by monitoring the electromotive force of the first detecting electrode 26 and the electromotive force of the second detecting electrode 27. For example, as shown in FIGS. 3 (c) and 3 (d), a time difference $t_a$ can be obtained from a time $t_2$ when the electromotive force of the second detecting electrode 27 decreases to 400 mV and a time $t_3$ when the electromotive force of the first detecting electrode 26 decreases to 400 mV.

Alternatively, the difference between the times when the oxygen gas has reached the first detecting electrode 26 and the second detecting electrode 27 can be obtained by monitoring a potential difference between the first detecting electrode 26 and the second detecting electrode 27. For example, in FIG. 3 (e), a time difference $t_b$ can be obtained from a time $t_4$ when the potential difference between the first detecting electrode 26 and the second detecting electrode 27 increases to 50 mV and a time $t_s$ when this potential difference decreases to 50 mV.

Figure 3A:
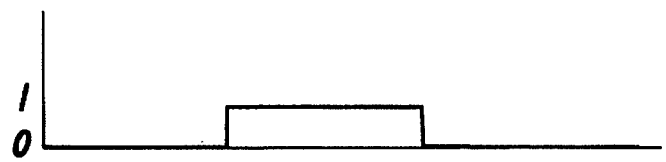
FIGS. 3(a), 3(b), 3(c), 3(d) and 3(e) are illustrative views of operation of the carbon monoxide sensor according to the present invention.
Figure 3B:
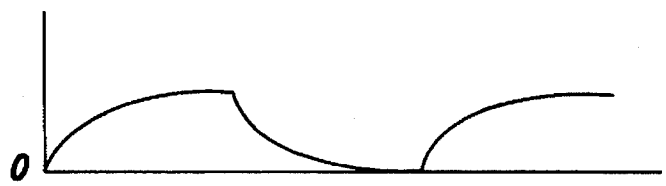
Figure 3C:
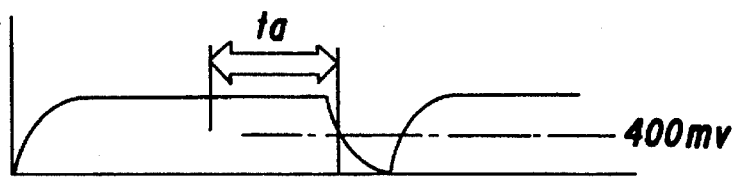
Figure 3D:
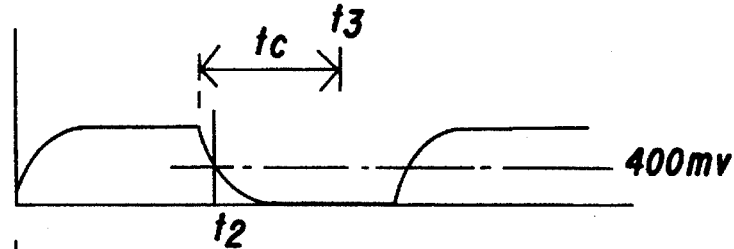
Figure 3E:
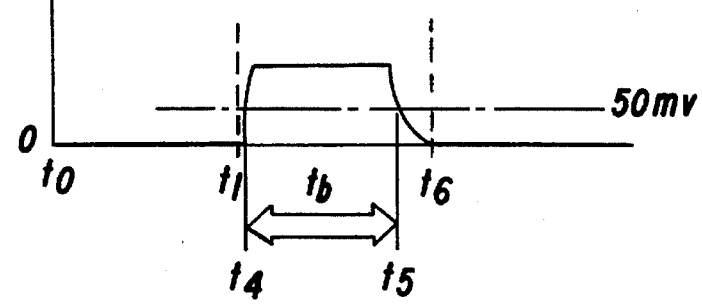
Figure 4:
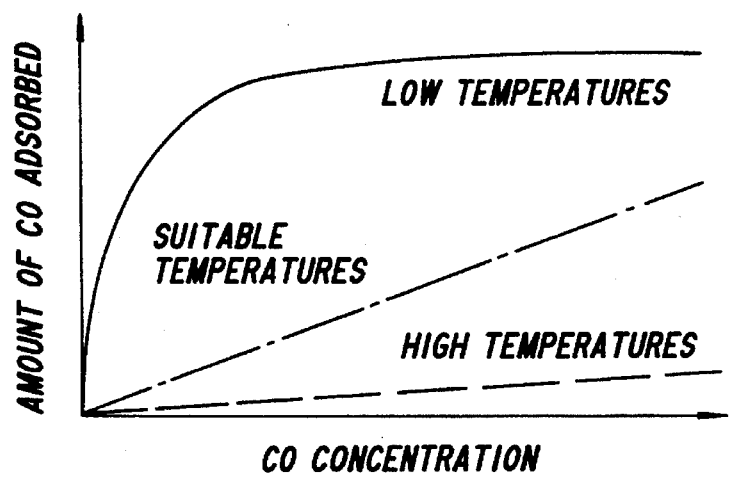
FIG. 4 is a graph showing a relation between the concentration of carbon monoxide in a gas to be measured and an amount of carbon monoxide absorbed by the carbon monoxide adsorbent.

FIG. 4 shows a relation between the concentration of carbon monoxide in the gas to be measured and the amount of carbon monoxide adsorbed onto the carbon monoxide adsorbent. High temperatures of the carbon monoxide adsorbent limit the amount of carbon monoxide adsorbed. However, at high temperatures, an amount of carbon monoxide adsorbed is proportional to a concentration of carbon monoxide until the concentration reaches to a certain high level. On the other hand, at a low temperature of the carbon monoxide adsorbent the carbon monoxide adsorbent is easily saturated with carbon monoxide. Therefore, at low temperatures, only a low concentration of carbon monoxide can be measured. However, in the low concentration region at low temperatures, a sensitivity in detecting a small amount of carbon monoxide is high. Therefore, temperatures of the carbon monoxide adsorbent may be changed as a means of varying the sensitivity and concentration measurement range, depending on concentrations of carbon monoxide. The measurement range may also depend on an amount and a type of the carbon monoxide adsorbent.

A third detecting electrode (not shown) may be preferably disposed in the first space 13a. A feedback circuit, including the third detecting element, for controlling the current or voltage of the pump cell may preferably be used so as to keep constant an electromotive force of the third detecting electrode to the reference electrode 28. Thus, a constant electromotive force of the third detecting electrode keeps the concentration of oxygen in the first space 13a constant.

In both of the method for measuring the concentration of carbon monoxide using the third space and the method using the second space and the third space, as shown in FIG. 3 (a), there are a period of a rich atmosphere being free from the oxygen gas and another period of a lean atmosphere containing the oxygen gas during one measurement cycle. Thus, it is preferable to repeat the cycles of the rich atmosphere and the lean atmosphere so as to average the times, thereby improving the accuracy in measuring the times.

Figure 8:
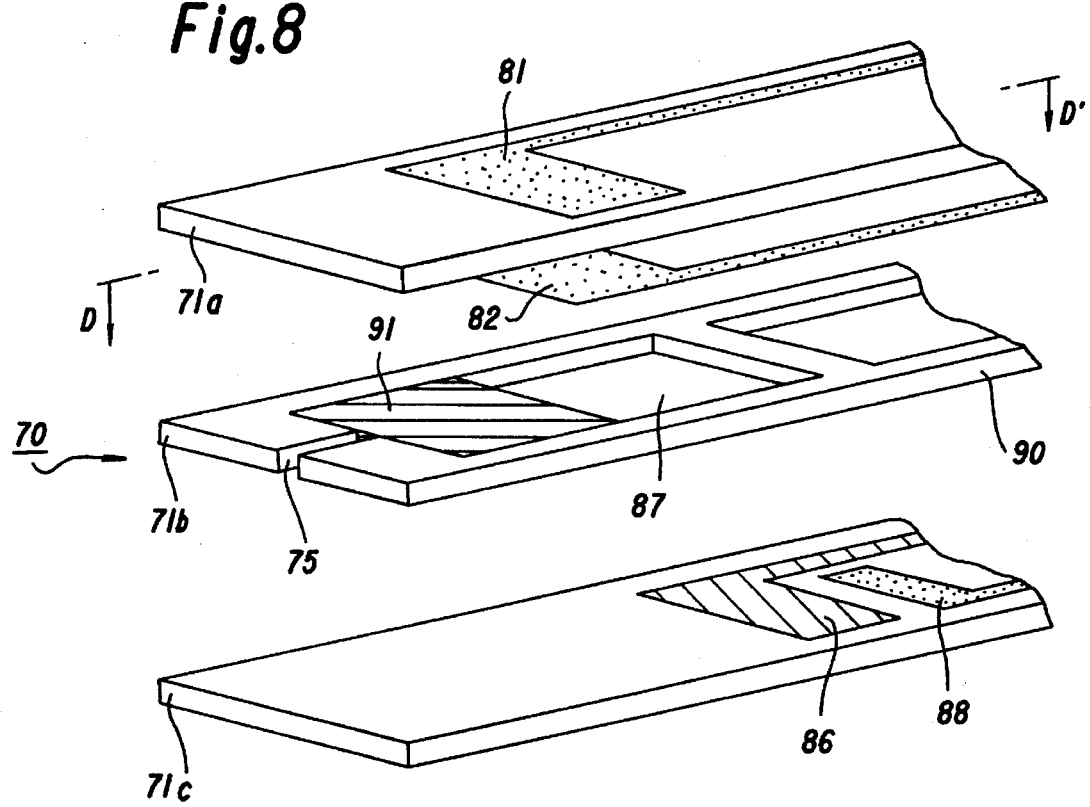
FIG. 8 is an exploded perspective view of a carbon monoxide sensor 70 which is still another embodiment of the present invention.
Figure 9:
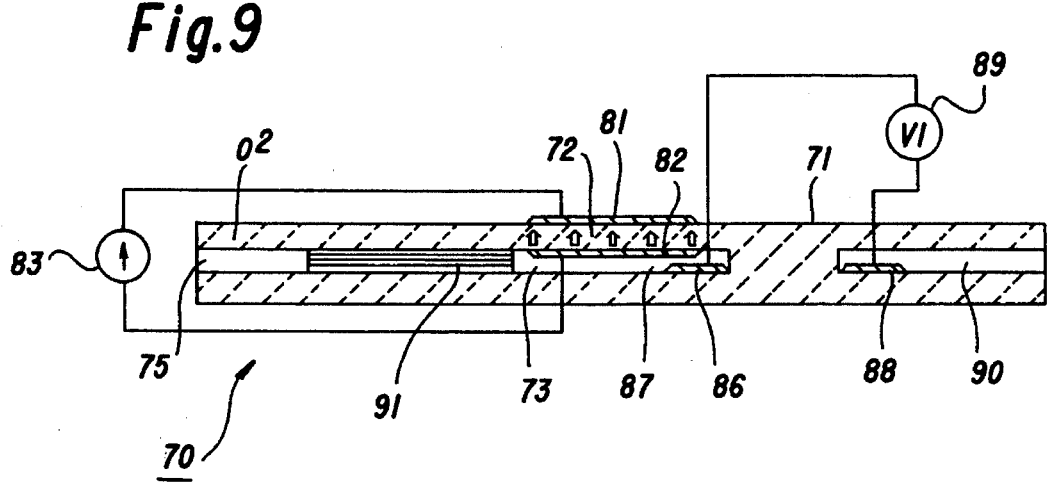
FIG. 9 is a sectional view cut along the line D–D' in FIG. 8.

FIG. 8 is an exploded perspective view of a carbon monoxide sensor 70 which is still another embodiment of the present invention. FIG. 9 is a sectional view cut along the line D–D' in FIG. 8.

The carbon monoxide sensor 70 has a substrate 71 defining a chamber 73, electrodes 81, 82, a first detecting electrode 86 and a reference electrode 88.

The substrate 71 has an integral structure including three sheets 71a, 71b, 71c, as in the substrate 41. The substrate 71 defines the chamber 73 inside thereof. The chamber 73 is partially filled with a carbon monoxide adsorbent 91. In contrast to the carbon monoxide sensor 40, the carbon monoxide adsorbent 91 is arranged on an aperture side 75 of the chamber 73 leaving an enclosed space 87 in the chamber 73. A first detecting electrode 86 is arranged on an inner surface of the substrate 71 defining the enclosed space 87. The carbon monoxide adsorbent 91 communicates with the ambiance through the aperture 75 of the substrate 71 so as to introduce a gas to be measured into the chamber 73. The aperture 75 can determine a diffusion rate of the gas into the chamber 73.

The gas to be measured passes through the aperture 75 and the carbon monoxide adsorbent 91 and then reaches the first detecting electrode 86 in the enclosed space 87 in the chamber 73, thereby the first detecting electrode 86 detects a partial pressure of oxygen in the gas.

As in the case of the pump cell of the carbon monoxide sensor 40, a pump cell of the carbon monoxide sensor 70 includes a pair of electrodes 81, 82 and a cell part 72 which is a part of the substrate 71. The pump cell can control a concentration of oxygen in the enclosed space 87 in the chamber 73. The cell part 72 is placed between the pair of electrodes 81, 82 so that oxygen ions may permeate the cell part 72. The electrodes 81, 82 and a power source 83 are similar to the electrodes 51, 52 and the power source 53, respectively.

The first detecting electrode 86 for detecting a partial pressure of oxygen in the space 87 is arranged on an inner surface of a solid electrolyte defining the space 87, whereby the first detecting electrode 86 can detect the partial pressure of oxygen in the gas which has passed through the carbon monoxide adsorbent 91.

The other elements of the carbon monoxide sensor 70 are similar to those of the carbon monoxide sensor 40. For example, reference numeral 89 refers to a voltmeter for measuring a potential difference between the reference electrode 88 and the first detecting electrode 86. A cavity 90 is formed in the substrate 71, and the cavity 90 is exposed to a gas other than the gas to be measured, for example, the atmosphere.

The usage of the carbon monoxide sensor 70 of the present embodiment will be described hereinafter.

The oxygen gas in a gas in the enclosed space 87 is substantially removed by the pump cell, while the carbon monoxide in the gas is adsorbed onto the carbon monoxide adsorbent 91. Then, the oxygen gas is introduced to the space 87 by the pump cell so that the oxygen gas reacts with carbon monoxide adsorbed onto the adsorbent 91, consuming the oxygen gas. The concentration of the oxygen gas in the space 87 remains stable while the first detecting electrode 86 keeps detecting partial pressures of oxygen. After all of the carbon monoxide adsorbed onto the adsorbent 91 reacts with the introduced oxygen gas, a partial pressure of oxygen in the space 87 begins to increase. Then, a period of time is measured from the introduction to the oxygen gas by the pump cell to the beginning of increasing the partial pressure of the oxygen, thereby converting the period into the concentration of carbon monoxide in the gas.

In the carbon monoxide sensor 70 of the present invention, the carbon monoxide adsorbent 91 is arranged on an aperture side in the chamber 73. Therefore, a diameter of the aperture 75 is preferably small so as to decrease disturbance to the adsorbent 91 from the atmosphere.

The carbon monoxide sensor of the present invention includes a pump cell for removing an oxygen gas in a sample, thereby the oxygen in the sample does not affect the accuracy in measuring a carbon monoxide concentration. Moreover, the sensor measures a time, thereby being less prone to an electrical noise, improving the accuracy in measuring the carbon monoxide concentration.

What is claimed is:

1. A carbon monoxide sensor comprising:

a substrate arranged with other adjacent or overlaid layers attached thereon and defining a bounded space into which an unknown gas or gas mixture to be measured is introduced, said substrate consisting essentially of a partially stabilized zirconia including $ZrO_2$ and a stabilizer chemical species or compound component;

a controlling means for controlling a partial pressure of oxygen in the bounded space;

an adsorbent, disposed in the bounded space, for adsorbing carbon monoxide;

a first detecting means for detecting a partial pressure of oxygen in the bounded space; and means for determining the concentration of carbon monoxide in said unknown gas or gas mixture based on the detection of the partial pressure of oxygen in the bounded space.

2. A carbon monoxide sensor of claim 1, wherein the bounded space comprises a first space into which said unknown gas or gas mixture is introduced and a second space in fluid communication with the first space, said controlling means controls a partial pressure of oxygen in the first space, said adsorbent is disposed on the second space and separates said first space from said first detecting means, and said first detecting means detects a partial pressure of oxygen in said adsorbent.

3. A carbon monoxide sensor of claim 2, wherein said carbon monoxide sensor further comprises a detector for detecting a partial pressure of oxygen in the first space.

4. A carbon monoxide sensor of claim 2, wherein the space further comprises a third space in fluid communication with said first space and separated from said second space and used for conducting a reference measurement of time for oxygen to flow from said first space through said adsorbent to said first detecting means, and the carbon monoxide sensor further comprises a second detecting means for detecting a partial pressure of oxygen in the third space so as to provide a reference signal output corresponding to said reference measurement time.

5. A carbon monoxide sensor of claim 1, wherein said controlling means comprises:

a solid electrolyte for conducting oxygen ion, said solid electrolyte is at least a part of said substrate; and a pair of electrodes for polarizing or pumping said solid electrolyte by placing said solid electrolytes between said electrodes.

6. A carbon monoxide sensor of claim 5, wherein said electrode comprises a film including a metal.

7. A carbon monoxide sensor of claim 1, wherein said substrate further comprises a bounded cavity isolated from said bounded space and in fluid communication with the ambient atmosphere near said sensor for conducting a reference measurement of oxygen partial pressure in said ambient atmosphere, a reference electrode disposed in the cavity for providing a reference measurement of oxygen partial pressure signal corresponding to said reference, and a monitoring means for monitoring a potential of said first detecting means based on said reference electrode.

8. A carbon monoxide sensor of claim 2, wherein said substrate includes an aperture for introducing a gas to be measured into the first space.

9. A carbon monoxide sensor of claim 1, wherein said adsorbent contains at least one of ZnO, $SnO_2$ and $Al_2O_3$, and said adsorbent is porous.

10. A carbon monoxide sensor of claim 2, wherein said first detecting means comprises a first detecting electrode.

11. A carbon monoxide sensor of claim 4, wherein said second detecting means comprises a second detecting electrode.

12. A method for detecting a concentration of carbon monoxide in an unknown gas or gas mixture comprising the steps of:

substantially removing an oxygen gas in said unknown gas or gas mixture in a first space by a controlling means for controlling a partial pressure of oxygen in a first space so that carbon monoxide in the gas is adsorbed onto an adsorbent for adsorbing carbon monoxide without any significant chemical interference due to local oxygen gas concentration in said adsorbent, said adsorbent being disposed in a second space that is in fluid communication with the first space;

increasing a partial pressure of oxygen in the first space by said controlling means so as to promote an oxidation reaction of the adsorbed carbon monoxide gas into carbon dioxide gas and free hydrogen ions;

measuring a response time that depends on said oxidation reaction before the oxygen gas in the first space reaches a first detecting means for detecting a partial pressure of oxygen in said adsorbent; and converting said measured response time into a carbon monoxide concentration in the unknown gas or gas mixture.

13. A method for detecting a concentration of carbon monoxide in an unknown gas or gas mixture comprising the steps of:

substantially removing an oxygen gas in said gas in a first space by a controlling means for controlling a partial pressure of oxygen in the first space so that carbon monoxide in the gas is adsorbed onto an adsorbent for adsorbing carbon monoxide without any significant chemical interference due to local oxygen gas concentration in said absorbent, said adsorbent being disposed in a second space that is in fluid communication with the first space;

increasing a partial pressure of oxygen in the first space by the controlling means so as to promote an oxidation reaction of the adsorbed carbon monoxide gas into carbon dioxide gas and free hydrogen ions;

measuring a time difference between a response time that depends on said oxidation reaction before the oxygen gas in the first space reaches a first detecting means for detecting a partial pressure of oxygen in said adsorbent and a reference time that the oxygen gas in the first space reaches a second detecting means for detecting a partial pressure of oxygen in a third space that is in fluid communication with the first space and separated from the second space; and converting said measured time difference into a carbon monoxide concentration in the unknown gas or gas mixture.

\* \* \* \* \*